United States Patent

Haseyama et al.

Patent Number: 5,159,045
Date of Patent: Oct. 27, 1992

[54] POLYISOCYANATO-ISOCYANURATE, AND PREPARATION PROCESS AND USE OF THE SAME

[75] Inventors: Ryuji Haseyama, Kanagawa; Kouzou Hayashi, Yamaguchi; Kazuyuki Kuroda, Fukuoka; Taisaku Kano; Takayoshi Sekido, both of Kanagawa; Hiroshi Nomura; Kiyoshi Shikai, both of Tokyo, all of Japan

[73] Assignees: Mitsui Toatsu Chemicals, Inc.; Shimizu Seiko Kabushiki Gaisha, Tokyo, Japan

[21] Appl. No.: 700,803

[22] Filed: May 16, 1991

[30] Foreign Application Priority Data

May 24, 1990 [JP] Japan .................. 2-132709
Jun. 22, 1990 [JP] Japan .................. 2-162595
Aug. 17, 1990 [JP] Japan .................. 2-215839

[51] Int. Cl.$^5$ .................................. C08G 18/80
[52] U.S. Cl. .................................. 528/45; 528/67; 528/49; 252/182.21
[58] Field of Search ............ 528/45, 67, 49; 252/182.21

[56] References Cited

U.S. PATENT DOCUMENTS 4,789,705  12/1988  Kase et al. .................. 528/67

FOREIGN PATENT DOCUMENTS 0039864   5/1981  European Pat. Off. .
0111189  11/1983  European Pat. Off. .
0193828   2/1986  European Pat. Off. .
0224165  11/1986  European Pat. Off. .
52-50786  12/1977  Japan .
57-7472    1/1982  Japan .

*Primary Examiner*—Maurice J. Welsh
*Attorney, Agent, or Firm*—Burns, Doane, Swecker & Mathis

[57] ABSTRACT

Polyisocyanato-isocyanurate and mixture of the same obtained by trimerizing straight chain aliphatic diisocyanate represented by the formula:

$$OCN-R_4-NCO$$

wherein $R_4$ is an alkylene group having 2-12 carbon atoms and polycyclo-aliphatic diisocyanate represented by the formula:

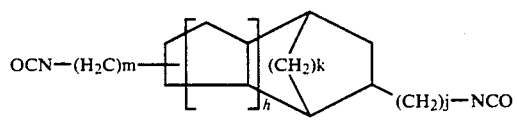

wherein k is an integer of 0 to 2, j and m are integers of 1 to 5, and h is an integer of 0 to 2; powder-paint curing agent which contains blocked isocyanate obtained by reacting the above raw materials with a blocking agent having at least one active hydrogen in a molecule; non-yellowing urathane paint resin prepared from the above raw materials and compound having at least two active hydrogen in a molecule; and paint composition comprising the curing agent and the resin; is disclosed.

35 Claims, No Drawings

POLYISOCYANATO-ISOCYANURATE, AND PREPARATION PROCESS AND USE OF THE SAME

BACKGROUND OF THE INVENTION

1. Field of the Invention

The present invention relates to a novel polyisocyanatoisocyanurate, and preparation process and use of the same. More particularly, the invention relates to a polyisocyanato-isocyanurate having a novel structure and preparation process of the same, and curing agent, resin and uses for paint of the polyisocyanato isocyanurate.

2. Description of Related Prior Art

Polyisocyanato-isocyanurate compounds obtained by trimerizing a part of isocyanate groups in organic diisocyanates and preparation process of the same have been known in many publications, for example, J. H. Saunders and K. C. Frish: Polyurethanes, Chemistry and Technology, page 94 (1962). These polyisocyanato-isocyanurate compounds are widely used for the materials of resin, foam, paint, film and adhesive.

For example, an isocyanurate compound of hexamethylene diisocyanate represented by the following formula (a):

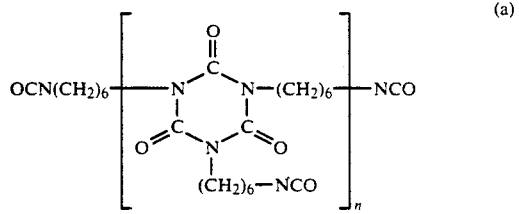

is used in various fields as a two-package type urethane paint resin and its raw material.

Two-package type urethane paint resins use isocyanate compounds as a curing agent and polyol compounds as a main component and are already used as various paints in many fields. However, paints having further excellent properties have been developed.

For example, an urethane type polyisocyanate or an isocyanurate type polyisocyanate which is derived from tolylene diisocyanate have been used for the curing agents, and alkyd resins, polyester polyols, acryl polyols or epoxy polyols have been used for the main component. Such a general purpose curing resin is most typically a two-package type urethane paint resin and is used for furniture and woodworking paints and for heavy duty anticorrosion tar-urethane paints.

Urethane paints derived from tolylene diisocyanate have high reactivity and excellent drying characteristics. However, weatherability is very poor.

In order to improve weatherability, it has been proposed for two-package type urethane paint resins to use aliphatic or alicyclic polyisocyanates derived from hexamethylene diisocyanate, isophoron diisocyanate or 4,4'-dicyclohexamethylene diisocyanate as a curing agent and to use acrylic polyol or polyester polyol as a main component.

Conventionally known curing agents for two-package type urethane paint resins are an urethane type polyisocyanates, biuret type polyisocyanates (for example, U.S. Pat. No. 3,903,127) and isocyanurate type polyisocyanate (for example, U.S. Pat. No. 3,487,080 and 4,412,073) which are derived from an aliphatic diisocyanate such as hexamethylene diisocyanate (hereinafter referred to as HDI); and urethane type polyisocyanates (for example, DE 1,962,808) and isocyanurate type polyisocyanates (for example, U.S. Pat. No. 3,919,218) which are derived from an alicyclic diisocyanate such as isophorone diisocyanate (hereinafter referred to as IPDI).

These polyisocyanates provide excellent characteristics such as weatherability, flexibility and abrasion resistance for the cured polyurethane paints and secure an immovable position in, for instance, the repair of automobiles and facing of buildings and structures.

These aliphatic or alicyclic polyisocyanates have poor drying characteristics. Consequently, the two package urethane paint obtained by using these polyisocyanates as curing agents have been required to stand for a long time or undergo forced drying process by baking in order to carry out sufficient crosslinking and form a tough film. However, poor heat resistance causes inevitable yellowing and loss of gloss in the baking step.

The polyisocyanato-isocyanurate derived from HDI has poor compatibility with polyols, acrylic polyol in particular. The two package urethane paint obtained by using these curing agents and main components lowers gloss, clarity and leveling properties and has the disadvantage of restricting the main component used.

The polyisocyanate derived from IPD1 has low reactivity because the isocyanate group to be reacted is bonded to a secondary carbon atom. Hence the two package urethane paint obtained by using the polyisocyanate as a curing agent has a disadvantage of very poor drying characteristics.

Further, polyisocyanato-isocyanurates derived from mixtures of HDI and IPD1 have been proposed in USP 4,419,513. In IPD1, however, one of the isocyanate groups is bonded to a primary carbon atom and has high reactivity, and the other isocyanate group is bonded to a secondary carbon atom and has low reactivity. When IPD1 is subjected to a ring-forming trimerization reaction, the isocyanate group of high reactivity preferentially reacts and that of low reactivity remains. Consequently, the polyisocyanato-isocyanurate obtained by trimerizing the mixture of HDI and IPD1 has low reactivity and leads to a urethane paint having poor drying characteristics. Even though a mixture containing an increased proportion of HDI is trimerized, the resulting polyisocyanato-isocyanurate leads to a yellowing at high temperature baking of the urethane paint thus obtained.

Therefore, it has been strongly desired to develop two-package type urethane paint resins having both good weatherability and excellent drying characteristics.

Further, so-called blocked isocyanates obtained by blocking the isocyanate group in the isocyanate compound is utilized as a curing agent for a polyester-based powder paint which employs polyester resin for the main component. The blocked isocyanate derived from IPD1 in particular, is commonly used, for example, for precoat metals as a polyester-based powder paint using polyester resin as the main component. When the blocked isocyanate derived from IPD1 is used for the curing agent, a baking temperature of 200° C. or above is usually required. Even though a metal catalyst such as dibutyltin dilaurate is used in combination, a baking temperature of 180° C. or above has been required. Consequently, a curing agent which has curing activity at decreased temperature and provides weatherability for the polyester-based powder paint has been desired.

SUMMARY OF THE INVENTION

A first object of the invention is to provide a novel polyisocyanato-isocyanurate and a mixture of the same which are useful for a urethane paint resin and other applications.

A second object of the invention is to provide a process for preparing the novel polyisocyanato-isocyanurate and the mixture of the same.

A third object of the invention is to provide a urethane paint resin having improved curing and drying characteristics and a paint composition comprising the resin by using the novel polyisocyanatoisocyanurate or the mixture of the same.

A fourth object of the invention is to provide a curing agent of polyester powder paint having excellent curing characteristics at decreased temperature and a polyester powder paint composition comprising the curing agent.

The present inventors have carried out extensive investigations on isocyanurate group containing polyisocyanates derived from various aliphatic diisocyanates in order to achieve the above objects. As a result, they have found that a polyisocyanatoisocyanurate and a mixture of the same which are prepared from a mixture of aliphatic diisocyanate represented by the formula (III) and polycyclo-aliphatic diisocyanate represented by the formula (IV) can be used as a curing agent for the preparation of urethane paint which has good weatherability and flexibility of film and has excellent in curing and drying characteristics. They have further found that a blocked isocyanate obtained by blocking isocyanate groups of particularly 2,5- or 2,6-diisocyanatomethyl-bicyclo [2,2,1] heptane and a mixture or a modified compound of the same, with a blocking agent having one or more active hydrogen in the molecule can exhibit excellent effects as a curing agent of polyester powder paint.

One aspect of the present invention is a mixture of a polyisocyanato-isocyanurate comprising two or more polyisocyanatoisocyanurates represented by the formula (I):

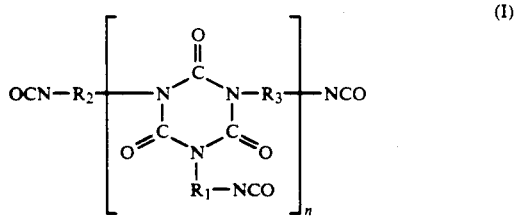

wherein $R_1$, $R_2$ and $R_3$ are alkylene groups having from 2 to 12 carbon atoms or groups represented by the formula (II):

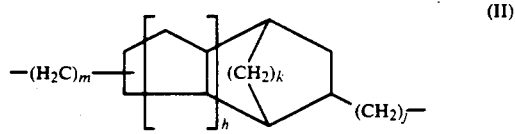

wherein k is an integer of from 0 to 2, j and m are integers of from 1 to 5, h is an integer of from 0 to 2, $R_1$, $R_2$ and $R_3$ may be the same or different, and n is an integer of from 1 to 5.

Another aspect of the invention is an essentially single compound of a polyisocyanato-isocyanurate wherein at least one of $R_1$, $R_2$ and $R_3$ in the formula (I) is a group represented by the formula (II) and the remainders are alkylene groups having from 2 to 12 carbon atoms.

A further aspect of the invention is a preparation process of the polyisocyanato-isocyanurate or the mixture of the same (unless otherwise noted hereinafter, an essentially single compound and a mixture of polyisocyanato-isocyanurate are simply referred to as polyisocyanato isocyanurate) by reacting a straight chain aliphatic diisocyanate represented by the formula (III):

$$OCN-R_4-NCO \qquad (III)$$

wherein $R_4$ is an alkylene group having from 2 to 12 carbon atoms, with a polycyclo-aliphatic diisocyanate represented by the formula (IV):

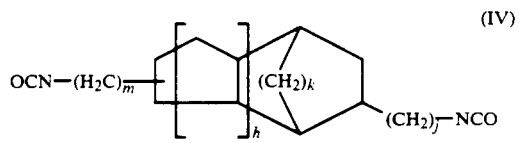

wherein k is an integer of from 0 to 2, j and m are integers of from 1 to 5, and h is an integer of from 0 to 2.

A still another aspect of the invention is a non-yellowing type urethane paint resin comprising the polyisocyanato-isocyanurate and a paint composition comprising the resin.

A still further aspect of the invention is a resin comprising an isocyanate group blocked with a blocking agent in the polyisocyanatoisocyanurate.

Another aspect of the invention is a curing agent of powder paint comprising a blocked isocyanate prepared by reacting particularly 2,5- or 2,6-diisocyanatomethyl-bicyclo [2,2,1] -heptane and a mixture or a modified compound of the same with the blocking agent having one or more active hydrogen in the molecule.

Characteristics of the polyisocyanato-isocyanurate of the present invention are as follows.

(1) Flowability and good workability is exhibited under 100% solid, that is, in the absence of a solvent and even at room temperatures.

(2) Isocyanate content is high and hence the proportion of the polyisocyanato-isocyanurate to polyol can be reduced.

(3) Heat stability is good because of the presence of an isocyanurate group, and development of hazardous isocyanate monomer due to decomposition is very small.

(4) A stable polycyclic structure is present in the skeleton.

The preparation process has good selectivity and can prepare the desired polyisocyanato-isocyanurate or the mixture of the same effectively with simple procedures.

The polyurethane paint obtained by using the polyisocyanatoisocyanurate as a curing agent is generally excellent in adhesion to various substrates, balance between hardness and flexibility, crack resistance, water resistance, chemical resistance, gloss and appearance and additionally has excellent weatherability, light stability and heat stability. For example, the polyisocyanatoisocyanurate of the invention has high reactivity and heat resistance as compared with an aliphatic polyisocyanato-isocyanurate derived from, for example, hexamethylene diisocyanate. Consequently, the non-yellowing type urethane paint resin of the invention obtained by using the polyisocyanato-isocyanurate has quick curing and drying ability in the initial stage, and yellowing in the baking step can be remarkably improved. The urethane paint thus obtained has good compatibility, excellent appearance and equivalent or superior film property to marketed paint, and hence is suitable for use in vehicle coating and other applications where workability, appearance and film properties are required.

When the blocked isocyanate prepared from 2,5- and/or 2,6-diisocyanatomethyl-bicyclo [2,2,1] heptane is used for the curing agent of powder paint, baking can be carried out at a decreased temperature of 160° C. in the conventional, curing agent/catalyst combination systems which require baking temperatures of 180° C. or more. The film of the powder paint thus obtained also has excellent weatherability.

DETAILED DESCRIPTION OF THE INVENTION

The essentially single compound or the mixture of polyisocyanato-isocyanurate of the present invention is included in the polyisocyanato-isocyanurate represented by the above formula (I). More particularly, the mixture of the polyisocyanato-isocyanurate is a mixture comprising more than two kinds of polyisocyanato-isocyanurate represented by the formula (I) wherein $R_1$, $R_2$ and $R_3$ are same or different and n is an integer of from 1 to 5. The essentially single compound of polyisocyanato-isocyanurate is a polyisocyanato-isocyanurate represented by the formula (I) wherein at least one of $R_1$, $R_2$ and $R_3$ is a group represented by the formula (II):

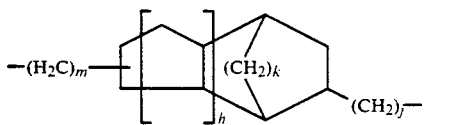

(II)

wherein k is an integer of from 0 to 2, j and m are integers of from 1 to 5, and h is an integer of from 0 to 2, and the remainders are alkylene groups having from 2 to 12 carbon atoms.

The above mixture of the polyisocyanato-isocyanurate of the invention can be obtained by trimerizing the mixture of the straight chain aliphatic diisocyanate represented by the formula (III) and the polycyclo-aliphatic diisocyanate represented by the formula (IV) under prescribed conditions in the presence of a trimerization catalyst.

That is, the preparation process of the present invention is characterized in trimerizing a portion of isocyanate groups comprised in the mixture of the straight chain aliphatic diisocyanate represented by the formula (III) and the polycycloaliphatic diisocyanate represented by the formula (IV) in a mole ratio of from about 11:1 to 1:11, conducting the reaction until trimerizing about 20 to 50% of initially present isocyanate groups, immediately adding a catalyst poison to terminate the trimerization reaction by deactivating the polymerization catalyst, and if desired, removing unreacted diisocyanate by thin film distillation.

The straight chain aliphatic diisocyanate which is used for the preparation process of the present invention is represented by the formula (III):

(III)

wherein $R_4$ is an alkylene group having from 2 to 12 carbon atoms.

Exemplary diisocyanates include
1,2-diisocyanatoethane,
1,3-diisocyanatopropane, 1,4-diisocyanatobutane,
1,5-diisocyanatopentane, 1,6-diisocyanatohexane,
1,7-diisocyanatoheptane, 1,8-diisocyanatooctane,
1,9-diisocyanatononane, 1,10-diisocyanatodecane,
1,11-diisocyanatoundecane and 1,12-diisocyanatododecane.

In these straight chain aliphatic diisocyanates, 1,6 diisocyanatohexane (hexamethylene diisocyanate, HDI) is commonly used in particular.

The polycycloaliphatic diisocyanate which is used in the process is represented by the formula (IV):

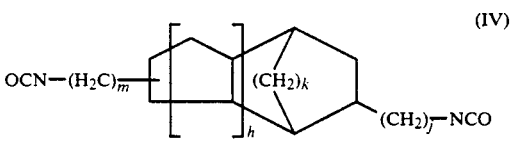

(IV)

wherein k is an integer of from 0 to 2, j and m are integers of from 1 to 5, h is an integer of from 0 to 2, and k=0 means no crosslinking.

Exemplary polycyclo-aliphatic diisocyanates having k=0 and h=0 include:
1,3-di(isocyanatomethyl)cyclohexane,
1,4-di(isocyanatomethyl)cyclohexane,
1,3-di(isocyanatoethyl)cyclohexane,
1,4-di(isocyanatoethyl)cyclohexane,
1-isocyanatomethyl-3(4)-isocyanatoethyl-cyclohexane,
1-isocyanatomethyl-3(4) isocyanatopropyl-cyclohexane,
1-isocyanatomethyl-3(4)-isocyanatobutyl-cyclohexane,
1-isocyanatomethyl-3(4)-isocyanatopentyl-cyclohexane,
1-isocyanatoethyl-3(4)-isocyanatopropyl-cyclohexane,
1-isocyanatoethyl-3(4)-isocyanatobutyl-cyclohexane, and
1-isocyanatomethyl-3(4)-isocyanatopentyl-cyclohexane.

Exemplary diisocyanates having k=0 and h=1 include:
3(4), 7(8)-di(isocyanatomethyl)bicyclo [4,3,0$^{1.6}$] nonane,
3(4)-isocyanatomethyl-7(8)-isocyanatoethylbicyclo[4,3,0$^{1.6}$] nonane,
3(4)-isocyanatoethyl-7(8)-isocyanatomethylbicyclo [4,3,0$^{1.6}$] nonane,
3(4)-isocyanatomethyl-7(8)-isocyanatopropylbicyclo [4,3,0$^{1.6}$] nonane,
3(4) isocyanatopropyl-7(8) isocyanatomethylbicyclo [4,3,0$^{1.6}$] nonane,
3(4)-isocyanatomethyl-7(8)-isocyanatobutylbicyclo [4,3,0$^{1.6}$] nonane, 3(4)-isocyanatobutyl-7(8)-isocyanatomethylbicyclo [4,3,0$^{1.6}$] nonane, 3(4)-isocyanatomethyl-7(8)-isocyanatopentylbicyclo [4,3,0$^{1.6}$] nonane, 3(4)-isocyanatopentyl-7(8)-isocyanatomethylbicyclo [4,3,0$^{1.6}$] nonane, 3(4),7(8)-di(isocyanatoethyl)bicyclo [4,3,0$^{1.6}$] nonane, 3(4)-isocyanatoethyl-7(8)-isocyanatopropylbicyclo [4,3,0$^{1.6}$] nonane, 3(4)-isocyanatopropyl-7(8)-isocyanatoethylbicyclo [4,3,0$^{1.6}$] nonane, 3(4)-isocyanatoethyl-7(8)-isocyanatobutylbicyclo [4,3,0$^{1.6}$] nonane, 3(4)-isocyanatobutyl-7(8)-isocyanatoethylbicyclo [4,3,0$^{1.6}$] nonane, 3(4)-isocyanatoethyl-7(8)-isocyanatopentylbicyclo [4,3,0$^{1.6}$] nonane, and 3(4)-isocyanatopentyl-7(8)-isocyanatoethylbicyclo [4,3,0$^{1.6}$] nonane.

Exemplary diisocyanates having $k=1$ and $h=0$ include:

2,5(6)-di(isocyanatomethyl)bicyclo [2,2,1] heptane, 2-isocyanatomethyl-5(6)-isocyanatoethylbicyclo [2,2,1] heptane, 2-isocyanatomethyl-5(6)-isocyanatopropylbicyclo [2,2,1] heptane, 2-isocyanatomethyl-5(6)-isocyanatobutylbicyclo [2,2,1] heptane, 2-isocyanatomethyl-5(6)-isocyanatopentylbicyclo [2,2,1] heptane, 2,5(6)-di(isocyanatoethyl)bicyclo [2,2,1] heptane, 2-isocyanatoethyl-5(6)-isocyanatopropylbicyclo [2,2,1] heptane, 2-isocyanatoethyl-5(6)-isocyanatobutylbicyclo [2,2,1] heptane, and 2-isocyanatoethyl-5(6)-isocyanatopentylbicyclo [2,2,1] heptane.

Exemplary diisocyanates having $k=2$ and $h=0$ include:

2,5(6)-di(isocyanatomethyl)bicyclo [2,2,2] octane, 2-isocyanatomethyl-5(6)-isocyanatoethylbicyclo [2,2,2] octane, 2-isocyanatomethyl-5(6)-isocyanatopropylbicyclo [2,2,2] octane, 2-isocyanatomethyl-5(6)-isocyanatobutylbicyclo [2,2,2] octane, 2-isocyanatomethyl-5(6)-isocyanatopentylbicyclo [2,2,2] octane, 2,5(6)-di(isocyanatoethyl)bicyclo [2,2,2] octane, 2-isocyanatoethyl-5(6)-isocyanatopropylbicyclo [2,2,2] octane, 2-isocyanatoethyl-5(6)-isocyanatobutylbicyclo [2,2,2] octane, and 2-isocyanatoethyl-5(6)-isocyanatopentylbicyclo [2,2,2] octane.

Exemplary diisocyantes having $k=1$ and $h=1$ include:

3(4),8(9)-di(isocyanatomethyl)tricyclo [5,2,1,0$^{2.6}$] decane,

3(4)-isocyanatomethyl-8(9)-isocyanatoethyltricyclo [5,2,1,0$^{2.6}$] decane,

3(4)-isocyanatomethyl-8(9)-isocyanatobutyltricyclo [5,2,1,0$^{2.6}$] decane,

3(4)-isocyanomethyl-8(9)-isocyanatopentyltricyclo [5,2,1,0$^{2.6}$] decane,

3(4)-isocyanomethyl-8(9)-isocyanatopentyltricyclo [5,2,1,0$^{2.6}$] decane,

3(4)-8(9)-di(isocyanatoethyl)tricyclo [5,2,1,0$^{2.6}$] decane,

3(4)-isocyanatoethyl-8(9)-isocyanatopropyltricyclo [5,2,1,0$^{2.6}$] decane,

3(4)-isocyanatoethyl-8(9)-isocyanatobutyltricyclo [5,2,1,0$^{2.6}$] decane and

3(4)-isocyanatoethyl-8(9)-isocyanatopentyltricyclo [5,2,1,0$^{2.6}$] decane.

In these polycyclo aliphatic diisocyanates, 2,5(6) di(isocyanatomethyl)bicyclo [2,2,1] heptane (hereinafter referred to as BCHI) and 3(4), 8(9)-di(isocyanatomethyl)tricyclo [5,2,1,0$^{2.6}$] decane (hereinafter referred to as TCDI) are preferred in particular.

The compounds having the formula (IV) wherein $h=1, j=1$ and $k=1$ can be prepared from cyclopentadiene dimer successively by way of hydroformylation, a reductive-amination and phosgenation as disclosed in for example, DE P.3,018,198.7 and German Laid-Open Patent 1,645,595 and 2,819,980.

The compounds having the formula (IV) wherein $h=0, j=1$ and $k=1$ can be prepared by phosgenation of corresponding diamines as disclosed in U.S. Pat. No. 3,143,570.

The amounts of the straight chain aliphatic diisocyanate of the formula (III) and the polycyclo-aliphatic diisocyanate of the formula (IV) in the process of the invention is in the range of from 11:1 to 1:11 by mole ratio.

The mixture having the above mole ratio is used for the raw material diisocyanate. The polyisocyanato-isocyanurate obtained by reacting the mixture is a transparent, viscous, resinous liquid and the viscosity varies depending upon the mixing ratio of the raw material. For example, when BCHI and HDI are used as starting materials, the polyisocyanato-isocyanurate obtained from the above range of BCHI/HDI mole ratio has high flowability and heat stability.

In order to practice the present invention, the straight chain aliphatic diisocyanate and the polycyclo-aliphatic diisocyanate raw materials are mixed in the above range of mole ratio and subjected to trimerization reaction in the presence of a trimerization catalyst.

The trimerization catalysts which can be used in the invention include, for example, (1) hydroxides or organic weak acid salts of tetraalkyl ammonium such as tetramethyl ammonium, tetraethyl ammonium and tetrabutyl ammonium, (2) hydroxides or organic weak acid salts of hydroxyalkyl ammonium such as trimethylhydroxypropyl ammonium, trimethylhydroxyethyl ammonium, triethylhydroxypropyl ammonium and triethylhydroxyethyl ammonium, (3) alkali metal, tin, zinc, lead and other metal salts of aliphatic carboxylic acids such as acetic acid, caproic acid, octanoic acid and myristic acid, (4) aminosilyl group containing compounds such as hexamethyldisilazane, and (5) tertiary amines such as triethylamine, tributylamine, N,N-dimethylaniline, N-ethylpiperidine, N,N'-dimethylpiperazine, Mannich salt of phenol compounds, and N,N',N"-tris(dimethylaminopropyl)-hexahydro-sym-triazine.

Particularly preferred trimerization catalysts are a combination of alkali metal salts of carboxylic acid with polyalkylene oxide or alcohol and exhibits an excellent effect on the reactivity and reaction control. The alkali metal salts of carboxylic acid include, for example, alkali metal formate, alkali metal acetate, alkali metal propionate, alkali metal octoate and alkali metal benzoate. Potassium acetate is preferred in these compounds. Polyalkylene oxide includes, for example, polyethylene glycol and polypropylene glycol having a molecular weight of from 200 to 3000. Polyethylene glycol having an average molecular weight of 400 is preferred. 2 Ethylhexanol can be used as alcohol.

A particular restriction is imposed on the usage of these compounds for the trimerization catalyst. For example, the alkali metal salts of carboxylic acid are commonly used as a solution in polyalkylene oxide or alcohol.

The amount of the trimerization catalyst used is in the range of from 0.0001 to 5% by weight, preferably from 0.001 to 2% by weight for the mixture of raw material diisocyanate.

Auxiliary catalsyts which can be used in the reaction include, for example, alcohols such as ethylene glycol, 1,3-butanediol, neopentyl glycol, 2-ethyl 1,3-hexanediol, trimethylolpropane, polypropylene glycol and phenol. These alcohols may be added simultaneously with the trimerization catalyst. Alternatively, these alcohols may be previously reacted with the raw material diisocyanate to form urethane linkage and then transfered to the trimerization step. Polyhydric alcohols which can also be used for the modifier of polyisocyanurate in particular are ethylene glycol, 1,3-butanediol, neopentyl glycol, 2-ethyl-1,3-hexanediol, 2,2,4-trimethyl-1,3-pentanediol and trimethylolpropane. The auxiliary catalysts is preferably used in an amount almost equivalent to the amount of the trimerization catalyst.

Reaction can be carried out in the presence or absence of a solvent. The solvent must naturally be inert to the isocyanate group.

Reaction temperature is usually in the range of from 20 to 120° C., preferably from 50 to 90° C. The reaction is preferably carried out in an inert atmosphere such as nitrogen, helium and argon.

The progress of reaction can be checked by measuring the amount of unreacted raw material with NCO % determination or gas chromatography of the reaction mixture.

When the conversion reaction is in excess, the product causes a viscosity increase and compatibility reduction to the polyol. Hence, conversion degree of the reaction is lowered, the reaction is terminated while remaining unreacted raw materials, and thereafter raw materials are removed from the reaction mixture. Degree of conversion is usually selected so as to obtain unreacted raw material content of from 30 to 80% by weight.

When the reaction reaches to the desired degree of conversion, the reaction is terminated by the addition of a catalyst deactivator such as hydrogen chloride, sulfuric acid, phosphoric acid, p-toluenesulfonic acid, trifluorosulfonic acid and other acids, benzoyl chloride and acetyl chloride. The preferred amount of the deactivator is in the range of from 1.0 to 1.5 times the equivalent weight of neutralizing the alkali metal salt of carboxylic acid.

When the trimerization reaction is terminated, unreacted diisocyanate still remains and the reaction mixture is an almost colorless liquid having low viscosity. After terminating the reaction, deactivated catalyst is removed, if desired, and unreacted raw materials and the solvents are successively removed. The desired polyisocyanato-isocyanurate can be obtained after separating unreacted raw materials and solvents by thin film distillation or solvent extraction. Unreacted diisocyanate in the polyisocyanatoisocyanurate thus obtained is preferably separated so as to get the content of about 1% or less.

Whether the desired polyisocyanato-isocyanurate is obtained substantially in the form of a single compound or in the form of a mixture of the same is selected depending upon the object of use. GPC separation process is used in order to obtain the polyisocyanatoisocyanurate in the form of the single compound.

The viscosity of polyisocyanato-isocyanurate mixture differs depending upon the mole ratio of the isocyanate starting material. When the mole ratio of BCHI to HDI is from 1:11 to 11:1, the mixture has flowability at the room temperature.

No particular restriction is imposed upon the equipment for carrying out the trimerization reaction. Preferred equipment is a reaction vessel equipped with a thermometer, nitrogen inlet tube and condenser and being capable of sufficiently stirring the reaction mixture.

The polyisocyanato-isocyanurate thus obtained is an essentially single compound or a mixture of two or more polyisocyanato-isocyanurates, and is used as a curing agent for a non-yellowing type urethane paint resin, raw materials for resin or paint compositions.

The mixture of the polyisocyanato-isocyanurate thus obtained can also be, if desired, blocked at its isocyanate group with a blocking agent and mixed with an active hydrogen containing compound to prepare a non-yellowing two-package type urethane paint resin having excellent heat resistance and weatherability.

The blocking agent used is a compound having at least one active hydrogen in the molecule. Useful compounds for the blocking agent include, for example, phenol, cresol, xylenol, p-ethylphenol, o-isopropylphenol, p-tert-butylphenol, p-tert-octylphenol, thymol, p-naphthol, p-nitrophenol, p-chlorophenol and other phenols;

methanol, ethanol, propanol, butanol, ethylene glycol, methyl cellosolve, butyl cellosolve, methyl carbitol, benzyl alcohol, phenyl cellosolve, furfuryl alcohol, cyclohexanol and other alcohols; dimethyl malonate, diethyl malonate, ethyl acetoacetate and other active methylenes;

butyl mercaptan, thiophenol, tert-dodecyl mercaptan and other mercaptanes;

ε-caprolactam; acetanilide, acetanisidine, acetamide, benzamide and other acid amides;

succinimide, maleimide and other imides; diphenylamine, phenylnaphthylamine, aniline, carbazole and other amines; imidazole, 2-ethylimidazole and other imidazoles;

urea, thiourea, ethyleneurea and other ureas; phenyl N-phenylcarbamate, 2-oxazolidone and other carbamates; ethyleneimine and other imines;

formaldoxime, acetaldoxime, methyl ethyl ketoxime, cyclohexanoneoxime and other oximes; and sodium hydrogen sulfite, potassium hydrogen sulfite and other sulfites.

These compounds are suitably selected depending upon the object and use, and can also be used singly or in combination.

Blocking of the isocyanate group by these blocking agents can be accomplished by mixing with about equimolar amounts of the polyisocyanato-isocyanurate in the preparation step of the paint resin and by heating at temperature of from about 50° to about 130° C. while stirring the mixture.

The non-yellowing type urethane paint resin of the invention is a resin derived from the thus-obtained polyisocyanato isocyanurate represented by the above formula (I) or the polyisocyanatoisocyanurate obtained by blocking NCO groups and the compound having at least two active hydrogen atoms.

The at least two active hydrogen containing compound which is used for the formation of the resin includes compounds and polymers containing at least two active hydrogen in a molecule.

The compounds and polymers include, for example,
glycols such as ethylene glycol, propylene glycol, $\beta, \beta'$-dihydroxyethyl ether(diethylene glycol), dipropylene glycol, 1,4-butylene glycol, 1,3-butylene glycol, 1,6-hexamethylene glycol, neopentyl glycol, polyethylene glycol, polypropylene glycol, polypropylene-polyethylene glycol and polybutylene glycol;

alkane polyols such as glycerol, trimethylolpropane, hexanetriol, pentaerythritol, xylitol and sorbitol;

polyether polyols obtained by addition polymerization of a single compound or a mixture of alkylene oxide such as ethylene oxide, propylene oxide and 1,2-butylene oxide to a single compound or a mixture of polyhydric alcohols such as glycerol and propylene glycol or polyfunctional compounds such as ethylene diamine and ethanolamine;

polyester polyol resins obtained by a condensation reaction of dibasic acids which are a single compound or a mixture selected from the group consisting of succinic acid, adipic acid, sebacic acid, dimer acid, maleic anhydride, phthalic anhydride, isophthalic acid and terephthalic acid and other carboxylic acid, with polyhydric alcohols which are a single compound or a mixture selected from the group consisting of ethylene glycol, propylene glycol, diethylene glycol, dipropylene glycol, 1,4-butylene glycol, 1,3-butylene glycol, 1,6-hexamethylene glycol, neopentyl glycol, glycerol and trimethylolpropane;

acrylic polyols obtained by copolymerizing a polymerizable monomer (a) having at least one active hydrogen in a molecule with other monomers which are copolymerizable with the same ((b) and-/or (c)), mor especially, acrylic polyol resins obtained by condensation reaction of (a) a compound or a mixture selected from the group consisting of active hydrogen containing acrylic acid esters such as 2-hydroxyethyl acrylate, 2-hydroxypropyl acrylate and 2-hydroxybutyl acrylate, active hydrogen containing methacrylic acid esters such as 2-hydroxyethyl methacrylate, 2-hydroxypropyl methacrylate and 2 hydroxybutyl methacrylate, acrylic acid mono-ester or methacrylic acid mono-ester of glycerol, and acrylic acid monoester or methacrylic acid monoester of trimethylolpropane, with (b) a compound or a mixture selected from the group consisting of acrylic acid esters such as methyl acrylate, ethyl acrylate, isopropyl acrylate, n-butyl acrylate and 2-ethylhexyl acrylate, and methacrylic acid esters such as methyl methacrylate, ethyl methacrylate, isopropyl methacrylate, n-butyl-methacrylate, isobutyl methacrylate, n-hexyl methacrylate and dodecyl methacrylate, and/or (3)

a compound or a mixture selected from the group consisting of unsaturated carboxylic acids such as acrylic acid, methacrylic acid, maleic acid and itaconic acid, unsaturated amides such as acrylic amide, N-methylolacrylic amide and diacetoneacrylic amide, and other polymerizable monomers such as glycidyl methacrylate, styrene, vinyltoluene, vinyl acetate and acrylonitrile;

epoxy resins of novolak type, $\beta$-methylepichloro type, cyclooxirane type, glycidyl ether type, glycidyl ester type, glycol ether type, epoxylated unsaturated fatty acid type, epoxylated fatty acid ester type, polybasic carboxylic acid ester type, aminoglycidyl type, halogenated type and resorcinol type;

monosaccharides or derivatives thereof selected from fructose, glucose, saccharose, lactose or 2-methylglucoxide;

and aromatic or heterocyclic polyhydric alcohols such as trimethylolbenzene, tris(2-hydroxyethyl-)isocyanurate and others.

These active hydrogen containing compounds may be used singly or as a mixture.

These active hydrogen containing compounds can also be used in combination with one or more of other compounds which have at least two active hydrogen atoms and are selected from, for example, primary or secondary amines such as ethylenediamine, triethylenediamine, hexamethylenediamine, m-xylylenediamine, diaminodiphenylmethane, isophoronediamine, diethylenetriamine, alkylene oxide adducts of various alkylene polyamines, and N,N'-dimethylethylenediamine; substituted urea compounds such as N,N'-dimethylurea and N-methyl-N'-cyclohexylurea;

thiolgroup containing compounds such as 1,2-ethanedithiol, 1,6-hexanedithiol, polyetherpolythiol and polyester polythiol;

carboxyl group containing compounds such as succinic acid, adipic acid, sebacic acid, terephthalic acid and carboxyl terminated polybutadiene;

or compounds having different active hydrogen containing groups in a molecule such as monoethanolamine, thioethanolamine, lactic acid and $\beta$-alanine.

The active hydrogen containing compounds for use in the invention are not limited to the compounds illustrated above. Any compound can be used so long as the compound can react with the polyisocyanato-isocyanurate used for the non-yellowing type urethane paint resin of the invention to form a urethane resin. Various combinations can be selected. Methyl ethyl ketoxime is preferably and frequently used in the active hydrogen containing compounds exemplified above.

In the formation of the non-yellowing type urethane paint resin of the invention, the compound having at least two active hydrogen atoms and the polyisocyanato-isocyanurate are blended so as to obtain an active hydrogen/NCO equivalent ratio of from 0.5 to 2, preferably from 0.8 to 1.2.

In preparing the non-yellowing type urethane paint resin, the compound having at least two active hydrogen atoms and the polyisocyanato-isocyanurate can be used, if desired, together with a suitable solvent which is selected depending upon the object and use.

Useful solvents include, for example, hydrocarbons such as benzene, toluene, xylene, cyclohexane, mineral spirit and naphtha;

ketones such as acetone, methyl ethyl ketone and methyl isobutyl ketone;

and esters such as ethyl acetate, n-butyl acetate, cellosolve acetate and isobutyl acetate. These solvents are used singly or as a mixture.

Catalysts, pigments, leveling agents, antioxidants, flame retardants, plasticizers, surfactants and other additives which are used in the art can be added depending upon the object and use.

In an embodiment for forming the non-yellowing type urethane paint resin by the present invention, a composition comprising the polyisocyanato-isocyanurate and the active hydrogen containing compound is prepared just before formation of the polyurethane resin, and the solvent and the additive are added, if desired. The polyurethane resin is usually formed by heating in the range of from room temperature to 150° C., and the polyurethane resin containing composition can be obtained. Alternatively, the isocyanate group of the polyisocyanato-isocyanurate is blocked with a blocking agent. Thus obtained blocked polyisocyanato-isocyanurate is blended with the active hydrogen containing compound and further mixed, if desired, with a solvent, catalyst, pigment, leveling agent, antioxidant, plasticizer, surfactant and other additives used in the art. Thus-obtained obtained mixture is heated in the range of from 100° to 250° C. to form the polyurethane resin containing composition.

The non-yellowing urethane paint prepared by using the resin of the invention exhibits excellent adhesion to substrates such as metal, plastic, rubber, leather and concrete, and hence can be utilized for a wide use as a paint of vehicles, installation and equipment, structural material and wood work.

The curing agent of powder paint in the invention is a blocked isocyanate prepared by reacting 2,5- and/or 2,6-diisocyanatomethylbicyclo [2,2,1] heptane or a modified derivative of the same with a blocking agent having at least one active hydrogen atom in the molecule. The powder paint obtained by using the curing agent is excellent in decreased temperature curing ability and weatherability.

The term "2,5- and/or 2,6-diisocyanatomethylbicyclo [2,2,1]-heptane" (hereinafter referred to as BCHI) means a single compound or a mixture of 2,5-diisocyanatomethylbicyclo [2,2,1] heptane, 2,6-diisocyanatomethylbicyclo [2,2,1] heptane and also includes modified derivatives of these diisocyanates. The modified derivatives are urethane prepolymer which can be obtained by reacting excess BCHI with water, diol or polyols and has active isocyanate groups at the end of the molecular chain, or polyisocyanate which is obtained by trimerization of BCHI and has an isocyanurate linkage. The polyisocyanate obtained by trimerization of BCHI is particularly preferred within the above modified derivatives. The modified derivatives may be the mixture containing residual monomers.

Diols and polyols which can be used for preparing the above urethane prepolymer having active isocyanate groups at the end of the urethane prepolymer having active isocyanate groups at the end of the molecular chain include, for example, diols such as ethylene glycol, diethylene glycol, polyethylene glycol, propylene glycol, dipropylene glycol, polypropylene glycol, 1,3-butanediol, 1,4-butanediol, 1,6-hexanediol, neopentyl glycol and 3-methylpentanediol;

and polyols such as trimethylolpropane, glycerol, polyester polyol and epoxy polyol.

Further, the above BCHI or its modified derivative can also be used in combination with other known isocyanates. In such a case, the urethane prepolymer must be prepared so as to have terminal BCHI in view of curing ability at decreased temperatures.

Representative isocyanates which are known and can be simultaneously used, include, for example, aliphatic or alicyclic diisocyanates such as isophorone diisocyanate (IPD1) and hexamethylene diisocyanate (HDI);

aromatic diisocyanates such as tolylene diisocyanate (TDI) and diphenylmethane diisocyanate (MDI);

urethane modified derivatives, carbodiimide modified derivatives or isocyanurate modified derivatives of the above aliphatic, alicyclic or aromatic diisocyanates;

a modified derivatives of these adduct; polyisocyanates such as crude TDI and polymethylene polyphenylene polyisocyanate (polymeric MDI).

Useful blocking agents which have at least one active hydrogen atom in the molecule, include, for example, $\epsilon$-caprolactam, methyl ethyl ketoxime, methyl isobutyl ketoxime, cyclohexanone oxime, ethyl acetoacetate and phenol. Preferred blocking agents are $\epsilon$-caprolactam, methyl ethyl ketoxime, methyl isobutyl ketoxime and cyclohexanone oxime in view of storage stability of the powder paint.

The curing agent for use in the powder paint of the invention can be prepared by usual process from the above BCHI, modified derivatives and those mixture and the blocking agent having at least one active hydrogen atom in the molecule.

The curing agent for use in the powder paint of the invention can be employed for powder paint by formulating a polyester polyol and other additives.

The polyester powder-paint composition of the invention comprises the above curing agent of powder paint and polyester polyol. The proportion of the powder-paint curing agent to the polyester polyol represented by a H/NCO equivalent ratio is in the range of from 0.8 to 1.3, preferably from 0.9 to 1.2. The H/NCO equivalent ratio means an equivalent ratio of active hydrogen (H) of polyester polyol to the isocyanate group (NCO) to be dissociated by removing the blocking agent from the blocked polyisocyanato-isocyanurate at the baking temperature.

The above polyester polyol can be prepared by a condensation reaction of the above diols or polyols with polybasic acids, for example, phthalic anhydride, isophthalic acid, terephthalic acid, dimethylterephthalic acid, adipic acid, azelaic acid, sebacic acid, trimellitic anhydride and other polybasic acids which are generally used for polyester preparation. The polyester polyol used in the invention is required to have terminal hydroxyl groups at the ends of polymer chain, and hence must be prepared in excess of hydroxyl group as compared with carboxyl group.

Additives may be added to the powder-paint composition in addition to polyester polyol. These additives are inorganic fillers and pigments such as titanium dioxide, barium sulfate, calcium carbonate, iron oxide and talc; organic pigments such as phthalocyanine blue, phthalocyanine green and carbon black; and other auxiliary materials, such as surfactants, ultraviolet absorbers, antioxidants and hardening catalysts.

Conventional powder paint was required a baking temperature of 180° C. or above, even though hardening catalyst is used. Use of the powder-paint curing agent of the invention enables decreased temperature curing at 160° C. and provides a paint film having excellent weatherability.

The present invention will hereinafter be illustrated further in detail by way of reference examples, examples and comparative examples. However, these examples are intended to illustrate the invention and are not to be construed to limit the scope of the invention.

Percent in these examples means percent by weight.

REFERENCE EXAMPLE 1

Preparation of 2,5(6)-Diisocyanatomethyl-Bicyclo [2,2,1] Heptane (Hereinafter Referred to As BCHI)

A mixture of 687 g of isoamyl acetate and 2189 g of ortho-dichlorobenzene (hereinafter referred to as ODCB) was prepared as the solvent for salt forming and phosgenation (hereinafter referred to as solvent mixture). The proportion of ODCB in the solvent mixture was 76.1%.

In a 3 l four necked flask, 1126 g of the solvent mixture was charged and cooled with stirring to 5° C. by ice water bath. Hydrogen chloride gas was blown through the solvent mixture for 30 minutes at a rate of 1.6 Nl/min.

Separately 250.0 g (1.62 mole) of a mixture composed of about 60 % of 2,5-isomer and about 40% of 2,6 isomer of diaminomethyl bicyclo [2,2,1] heptane (hereinafter referred to as BCHA) were dissolved in 1750 g of solvent mixture. The solution thus obtained had a diamine concentration of 12.5%. The solution was added dropwise to the flask over 2 hours while continuing the cooling of flask to maintain internal temperature at 10° to 15° C.

Blowing of hydrogen chloride gas was continued at a rate of 1 Nl/min. After finishing the dropwise addition of the raw material diamine, blowing of hydrogen chloride gas was further continued at a rate of 0.4 Nl/min. for 2 hours while maintaining the internal temperature of the flask at 25° C. or less to complete the salt-forming reaction.

The salt-forming reaction was progressed very smoothly without developing block of hydrochloride particles to obtain a pale yellowish white, uniform slurry of fine particles.

After finishing the salt-forming reaction, the internal temperature of the flask was raised from 25° to 160° in 50 minutes. When the temperature was reached to 100° C., phosgene was slowly blown through the reaction mixture to start of a phosgenation reaction. Phosgen blowing was continued at a rate of 100 to 120g/hr while controlling the internal temperature at 160±1° C. with a mantle heater.

After blowing phosgene for about 6 hours, the reaction mixture changed from white slurry to almost clear solution. After blowing phosgene for further 30 minutes at a rate of 50g/hr, the phosgenation reaction was terminated. Overall phosgenation reaction time was 6.5 hours and the phosgene gas used was about 2.2 times the theoretical amount.

Thereafter, nitrogen gas was blown through the reaction mixture at a rate of 1.3 Nl/min for 80 minutes to carry out degassing while maintaining the temperature at 160±1° C. After degassing, the reaction mixture was cooled and filtered through a filter paper (1 μm) in order to remove a trace amount of solid components.

Solvent was removed from the filtrate and the residue was rectified under vacuum and 306.5 g of main fraction having a boiling point of 110°-116° C./0.4-0.6 torr was obtained.

The product had following analytical values.

| | |
|---|---|
| NCO content (%) | 40.72 |
| Hydrolyzable chlorine (%) | 0.032 |
| Purity by gas chromatography (%) | 99.8 |
| Hydrolyzable chlorine after solvent removal | 0.202 g/100 g BCHI |

| | Elementary analysis | | |
|---|---|---|---|
| | C | H | N |
| Calculated (%) | 64.06 | 6.84 | 13.58 |
| Found (%) | 64.11 | 6.89 | 13.47 |

The main fraction was BCHI, which was identified by elementary analysis, IR-spectrum and NMR-spectrum. The yield of the main fraction was 91.7% of the theoretical amount (1.62 mole, 334.2 g).

EXAMPLE 1

Preparation of Polyisocyanato-Isocyanurate By Ring-Forming Trimerization of a Mixture of 1,6-Hexamethylene Diisocyanate (Hereinafter Referred To As HDI) and BCHI (1) Preparation of a Catalyst Mixture (Hereinafter Referred to As Catalyst-A)

Catalyst-A was prepared by dissolving 1.0 g of dried, anhydrous potassium acetate in 9 g of polyethylene glycol having an average molecular weight of 400.

(2) Preparation of Polyisocyanato-Isocyanurate By Ring Forming Trimerization.

To a four necked flask equipped with a thermometer, condenser, nitrogen inlet tube and stirrer, 100 g(0.595 mole) of 1,6-hexamethylene diisocyanate, 100 g(0.485 mole) of BCHI and 1.6 g of catalyst-A were charged and heated to 80° C. After 2.5 hours, NCO content was decreased from 45.35% to 24.3%. Then 0.25 g of benzoyl chloride was added and stirred at 60° C. for an hour to deactivate trimerization catalyst-A. A pale yellow, transparent, viscous liquid was obtained.

The reaction mass thus obtained was subjected to thin film distillation under vacuum of 0.2 torr to remove unreacted raw materials. The polyisocyanato-isocyanurate mixture obtained was 110 g. The mixture was dissolved in 110 g of butyl acetate to obtain an polyisocyanato-isocyanurate solution having resin constants described below.

| Resin constant | |
|---|---|
| Appearance | light yellow, transparent |
| NCO content (%) | 9.25 |
| Viscosity (Gardner/25° C.) | D |
| Solid contents (%) | 50 |

The methyl carbamate compound obtained by reacting a portion of the solution with methyl alcohol had following polymer proportions by ger permeation chromatography(hereinafter referred to as GPC analysis)

| | |
|---|---|
| Polymer of n = 1 (trimer) | 66.3% |
| Polymer of n = 2 (pentamer) | 21.6% |

| -continued | |
|---|---|
| Polymer of n = 3 (heptamer) | 8.3% |
| Polymers of n = 4 and 5 | 3.8% |

According to the GPC analysis, almost no content was found on high polymers of n=6 or more and polyisocyanato-isocyanurate containing 30% or more of polymer of n=1.

The above methyl carbamate compound was newly subjected to GPC analysis to separate each component. An NMR spectrum and FD MS spectrum were measured and analyzed on the trimer fraction (polymer of n=1). On the analysis, a methyl carbamate compound was prepared from single polymer of BCHI and single trimer (single polymer of n=1) was separated by GPC. A spectrum was measured on the single trimer of BCHI thus obtained and used as a reference spectrum.

Mass numbers of 600, 638, 676 and 714 were detected by an FD-MS spectrum. Each of these mass numbers coincided with the molecular weight of the single trimer of BCHI, single trimer of HDI, co-trimer of BCHI and HDI in a molar ratio of 2:1, and co-trimer of BCHI and HDI in a molar ratio of 1:2, respectively. As a result of the above analyses, it was confirmed that the compound of the formula (I) was obtained.

The spectrum of $^{13}$C-NMR separately exhibited signals of methylene carbon in HDI(26.7 ppm, 30 ppm and 41 ppm), signals of bicyclo ring carbon in BCHI(28-47 ppm), and signals of carbonyl carbon in trimer ring (150 ppm), respectively. Thus, composition ratio of BCHI to HDI could be obtained from NNE mode of $^{13}$C-NMR.

EXAMPLE 2

Preparation of Polyisocyanato-Isocyanurate By Ring-Forming Trimerization of a Mixture of 1,6-Hexamethylene Diisocyanate and BCHI To a four necked flask equipped with a thermometer, condenser, nitrogen inlet tube and stirrer, a mixture composed of 140g(0.832 mole) of HDI and 60g(0.291 mole) of BCHI, and 1.5 g of catalyst-A were charged and heated to 80° C. After 4.0 hours, NCO content was decreased from 47.2% to 36.4%. Then 0.114 g of benzoyl chloride was added and stirred at 60° C. for an hour to deactivate trimerization catalyst-A. A pale yellow, transparent, viscous liquid was obtained.

The reaction mass thus obtained was subjected to thin film distillation under vacuum of 0.2 torr to remove unreacted raw materials. The polyisocyanato-isocyanurate mixture obtained was 65 g. The mixture was dissolved in 65 g of butyl acetate to obtain an polyisocyanato-isocyanurate solution having the resin constants described below.

| Resin constant | |
|---|---|
| Appearance | light yellow, transparent |
| NCO content (%) | 10.25 |
| Viscosity (Gardner/25° C.) | B |
| Solid contents (%) | 50 |

EXAMPLE 3

Preparation of Polyisocyanato-Isocyanurate By Ring-Forming Trimerization of a Mixture of 1.6-Hexamethylene Diisocyanate and BCHI To a four necked flask equipped with a thermometer, condenser, nitrogen inlet tube and stirrer, a mixture composed of 180g(1.070 moles) of HDI and 20g(0.097 mole) of BCHI, and 1.6 g of catalyst-A were charged and heated to 80° C. After 4.0 hours, NCO content was decreased from 49.1% to 34.7%. Then 0.114 g of benzoyl chloride was added and stirred at 60° C. for an hour to deactivate trimerization catalyst-A. A pale yellow, transparent, viscous liquid was obtained.

The reaction mass thus obtained was subjected to thin film distillation under vacuum of 0.2 torr to remove unreacted raw materials. The polyisocyanato-isocyanurate mixture obtained was 72 g. The mixture was dissolved in 72 g of butyl acetate to obtain an polyisocyanato-isocyanurate solution having resin constants described below.

| Resin constant | |
|---|---|
| Appearance | light yellow, transparent |
| NCO content (%) | 10.65 |
| Viscosity (Gardner/25° C.) | A |
| Solid contents (%) | 50 |

EXAMPLE 4

The same procedures as described in Example 2 were carried out except that 180g(1.144 moles) of BCHI and 20g(0.119 mole) of HDI were used. NCO content was decreased from 41.7% to 31.5%. Benzoyl chloride used as catalyst poison was 0.114 g. After thin film distillation, 86 g of a mixture of polyisocyanato-isocyanurate was obtained. The mixture had residual BCHI of 0.01%, residual HDI of trace, NCO content of 17.5%, and viscosity of 36.000 cps/25° C.

EXAMPLE 5

The procedures conducted in Example 1 were repeated by using 100g(0.406 mole) of TCDI, 100g(0.594 mole) of HDI and 1.5 g of catalyst-A. Reaction was carried out for 4 hours after increasing the temperature to 80° C. NCO content was decreased from 42.1% to 33.7%. Thereafter 0.21 g of benzoyl chloride was added and reaction was carried out at 60° C. for an hour. Unreacted diisocyanate monomer was removed from the reaction product by thin film distillation under vacuum of 0.2 torr. Polyisocyanato-isocyanurate mixture obtained was 73 g. The mixture had residual TCDI of 0.40%, residual HDI of 0.01% or less, and NCO content of 16.5%.

EXAMPLE 6

The same procedures as described in Example 5 were carried out except that 60g(0.244 mole) of TCDI and 140g(0.832 mole) of HDI were used. NCO content was decreased from 45.2% to 34.9%. Benzoyl chloride used as catalyst poison was 0.114 g. After thin film distillation, polyisocyanato-isocyanurate mixture obtained was 66 g. The product had residual TCDI of 0.40%, residual HDI of 0.01% or less, and NCO content of 17.3%.

EXAMPLE 7

Procedures conducted in Example 1 were repeated by using 20g(0.097 mole) of BCHI, 20g(0.08 mole) of TCDI, 160g(0.832 mole) of HDI and 1.5 g of catalyst-A. The reaction was carried out for 4 hours after increasing the temperature to 80° C. NCO content was decreased from 47.2% to 36.1%. Benzoyl chloride added was 0.114 g. Reaction was conducted for an hour at 60° C. Unreacted diisocyanate monomer was removed from the reaction product by thin film distillation under vacuum of 0.2 torr.

Polyisocyanato-isocyanurate mixture thus obtained was 68 g. The mixture had residual BCHI of 0.10%, residual TCDI of 0.30%, residual HDI of 0.01% or less, and NCO content of 19.0%.

EXAMPLE 8

The same procedures as described in Example 7 were carried out except that 50g(0.242 mole) of BCHI, 50g(0.203 mole) of TCDI, and 100g(0.594 mole) of HDI were used. NCO content was decreased from 43.7% to 34.1%. Benzoyl chloride used as catalyst poison was 0.114 g. After thin film destillation, polyisocyanato isocyanurate mixture obtained was 69 g. The mixture had residual BCHI of 0.10%, residual TCDI of 0.40%, residual HDI of 0.01% or less, and NCO content of 16.9%.

EXAMPLE 9

Preparation of Polyisocyanato-Isocyanurate By Ring-Forming Trimerization of BCHI To a four necked flask equipped with a thermometer, condenser, nitrogen inlet tube and stirrer, 200g(0.97 mole) of BCHI and 1.5 g of catalyst-A were charged and heated to 80° C. After 2 hours, NCO content decreased from 40.7% to 30.5%, and hence 0.114 g of benzoyl chloride was added and stirred at 60° C. for an hours to deactivate trimerization catalyst A. Pale yellow, transparent, viscous liquid was obtained.

The reaction mass thus obtained was subjected to thin film distillation under vacuum of 0.2 torr to remove unreacted raw materials. Polyisocyanato-isocyanurate mixture thus obtained was 80 g. The mixture was dissolved in 80 g of butyl acetate to obtain an polyisocyanato-isocyanurate solution having resin constants described below.

| Resin constant | |
| --- | --- |
| Appearance | light yellow, transparent |
| NCO content (%) | 8.50 |
| Viscosity (Gardner/25° C.) | E |
| Solid contents (%) | 50 |

COMPARATIVE EXAMPLE 1

Preparation of Polyisocyanato-Isocyanurate By Ring Forming Trimerization of a Mixture of HDI and IPDI To a four necked flask equipped with a thermometer, condenser, nitrogen inlet tube and stirrer, 100g(0.59 mole) of 1,6-hexamethylene diisocyanate, 100g(0.45 mole) of isophorone diisocyanate and 1.5 g of catalyst-A were charged and heated to 80° C. After 4 hours, NCO content was lowered to 34.7% and hence 0.215 g of benzoyl chloride was added and stirred at 60° C. for an hour to deactivate trimerization catalyst-A. Pale yellow, transparent, viscous liquid was obtained.

The reaction mass thus obtained was subjected to thin film distillation under vacuum of 0.2 torr to remove unreacted raw materials. Polyisocyanato-isocyanurate mixture thus obtained was 82 g. The mixture was dissolved in 82 g of butyl acetate to obtain a polyisocyanato isocyanurate solution having resin constants described below.

| Resin constant | |
| --- | --- |
| Appearance | light yellow, transparent |
| NCO content (%) | 9.12 |
| Viscosity (Gardner/25° C.) | D |
| Solid contents (%) | 50 |

EXAMPLE 10

Blocking Reaction

To 100 g of polyisocyanato-isocyanurate obtained by the same procedures as described in Example 1, 19.6g(0.23 mole) of methyl ethyl keto oxime was added and stirred at 80° C. for 3 hours. Isocyanate content was lowered to 0.02%. The reaction mixture was cooled to obtain blocked urethane having effective isocyanate content of 7.73%.

EXAMPLE 11-14 AND COMPARATIVE EXAMPLES 2-5

Paint film test was carried out by using the polyisocyanatoisocyanurate solutions obtained in Examples 1-3 and an acrylic polyol resin solution, OLESTER Q-182 (Trade mark of Mitsui Toatsu Chemicals Inc.), having a number average molecular weight of 9500, solid content of 50%, and hydroxyl value of 45 KOHmg/g.

(1) Preparation of Base Enamel

Base enamel of acrylic resin OLESTER Q-182 was prepared by the following method.

| | |
| --- | --- |
| Acrylic resin OLESTER Q-182 | 50 parts |
| Pigment: Titanium dioxide R-930 (manufactured by Ishihara Sangyo Co. Ltd.) | 50 parts |

Both components were blended in the above proportion and the pigment was incorporated into the resin by using a three-roll mill to prepare a base enamel.

(2) Paint Film Test

The polyisocyanato-isocyanurate solution obtained in Examples 1-3, acrylic polyol resin OLESTER Q-182, and the base enamel prepared in (1) were blended so as to obtain same equivalent of isocyanate group as hydroxyl group and a pigment weight concentration (PWC) of 40%. To the mixture obtained, a solvent mixture of ethyl acetate/toluene/butyl acetate/xylene/-cellosolve acetate in a ratio of 30/30/20/15/5 by weight was added as a thinner. The concentration of the mixture was adjusted to 15 seconds at 25° C. by Ford cup #4. Thus, non-yellowing type urethane paint resin of the present invention was obtained. The resin obtained was applied to a steel panel and a glass plate so as to obtain a dry film thickness of 25μm with a spray gun, IWATA model W-77, having a nozzle diameter of 2 mm. The coated films were allowed to stand for 7 days at 20° C. under relative humidity of 60%, and then subjected to tests.

For the purpose of comparison, the same tests were carried out by using the isocyanurate-polyisocyanate solutions obtained in Example 9 and Comparative Example 1 and also three kinds of conventional aliphatic polyisocyanate, that is, (1) a biuret derivative of hexamethylene diisocyanate OLESTER NP-1000 (Trade mark of Mitsui Toatsu Chemicals Inc.), (2) an isocyanurate derivative of hexamethylene diisocyanate CO-LONATE EH (Trade mark of Nippon Polyurethane Co. Ltd.), and (3) an isocyanurate derivative of isophorone diisocyanate IPDI T-1890 (Trade mark of Daicel Huels Co. Ltd.). Properties of paints and applied films are illustrated in Table 1.

Paint film test were carried out at 20° C. under relative humidity of 60% and evaluation was conducted in accordance with JIS K-5400.

Items (1)–(9) illustrated in the tables were carried out by the following test methods.

(1) Adhesion test . . . In accordance with JIS D-0202.

(2) Erichser extrusion . . . In accordance with JIS Z-2247.

(3) Magic staining properties . . . In accordance with JAS 1373.

A specimen is horizontally placed. A line having a width of 10 mm is drawn on the surface of a specimen with a quick drying ink specified in JIS 6037 (1964). After allowing to stand for 24 hours, the ink is wiped off with a cloth containing ethyl alcohol. The results are evaluated into the following three classes.

○ . . . No trace is found.
Δ . . . A faint trace is found.
X . . . A distinct trace is found.

(4) Xylene rubbing test (50 cycles)

A specimen is fixed on a rubbing fastness tester of dyed materials and rubbed back and forth 50 times with a cotton cloth containing 2 ml of xylene under load of 500 g. The results are evaluated into the following three classes.

○ . . . No trace is found.
Δ . . . A faint trace is found.
X . . . A distinct trace is found.

(5) Resistance to acids and alkalis . . . In accordance with JAS 1373.

A specimen is horizontally placed and a drop of a 10% aqueous sulfuric acid solution and a drop of a 10% sodium hydroxide solution are separately put on the specimen surface. The specimen is then covered with a watch glass for 24 hours and successively allowed to stand for 24 hours in the atmosphere at room temperature. Thereafter the specimen is washed with water and dried in the air. The results are evaluated into the following three classes.

○ . . . No trace is found.
Δ . . . A faint trace is found.
X . . . A distinct trace is found.

(6) WOM (weather-o-meter) yellowing degree . . . In accordance with JIS K-7103.

(7) Gloss (60° gloss) . . . In accordance with JIS K-5400.

(8) Du Pont impact test(½ in/500 g) . . . In accordance with JIS K-5400.

(9) Secondary physical properties

Measurement is conducted after immersing in boiling water for 4 hours.

EXAMPLE 15-18 AND COMPARATIVE EXAMPLE 6-9

Marketed polyester polyol resin OLESTER Q-173(Trade mark of Mitsui Toatsu Chemicals Inc.) having solid content of 100% and a hydroxyl value of 256 KOHmg/g were used.

Paint preparation and spray application were carried out by the same procedures as described in Preparation Example 11 and resulting paint film was forced to dry at 150° C. for 20 minutes and allowed to stand at 20° C. for 7 days under relative humidity of 60%. Thereafter the film was tested and evaluated by the same procedures as above. Result are summarized in Table 2.

REFERENCE EXAMPLE 2

Preparation of Acrylic Polyol Resin

A monomer mixture obtained by mixing 150 g of 2-hydroxyethyl methacrylate, 50 g methyl methacrylate, 150 g of n-butyl methacrylate, 25 g of n-butyl acrylate, 125 g of styrene, 15 g of acrylic acid, 25 g of diethylene glycol and 50 g of tert-butylperoxy-2-ethylhexoate were dropwise added continuously to 1200 g of n-butyl-acetate under stirring and refluxing, and further refluxed for 5 hours to carry out polymerization. After finishing polymerization a portion of n-butyl acetate was distilled off to adjust the solid content to 80%. The acrylic polyol resin solution thus obtained had viscosity of 6500 cps at 25° C., number average molecular weight of 1300 and hydroxyl value of 92 KOHmg/g.

REFERENCE EXAMPLE 3

A base enamel of the acrylic resin obtained in Reference Example 2 was prepared by the following formulation.

| | |
|---|---|
| The acrylic polyol resin in Reference Example 2 | 45 parts |
| Pigment: Titanium dioxide R-930 | 45 parts |
| (Trade mark of Ishihara Sangyo Co. Ltd.) | |
| Thinner: A mixed solution of xylene/toluene/ butyl acetate/methyl isobutyl ketone in a ratio of 30/30/20/20 by weight | 10 parts |

These components were blended in the above proportion and the pigment was incorporated into the resin by using a three-roll mill to prepare the base enamel.

EXAMPLE 19 AND COMPARATIVE EXAMPLE 10

The blocked urethane solution of polyisocyanato-isocyanurate obtained in Example 10, the acrylic polyol resin solution of Reference Example 2, and the base enamel prepared in Reference Example 3 were blended so as to obtain the same equivalent of effective isocyanate group as hydroxyl group and a pigment weight concentration (PWC) of 40%. To the mixture obtained, a solvent mixture of ethyl acetate/toluene/butyl acetate/xylene/cellosolve acetate in a ratio of 30/30/20/15/5 by weight was added as a thinner. The concentration of the mixture was adjusted to 15 seconds at 25° C. by Ford cup #4. Thus, non-yellowing type urethane paint resin of the present invention was obtained. The resin obtained was applied to a steel panel and a glass plate so as to obtain a dry film thickness of 25 μm with a spray gun, IWATA model W-77, having a nozzle diameter of 2 mm. The spray gun, IWATA model W-77, having a nozzle diameter of 2 mm. The coated films were forced to dry at 150° C. for 20 minutes and then allowed to stand for 7 days at 20° C. under relative humidity of 60 %. Thus obtained films were tested their properties by the same evaluation methods as above.

For the purpose of comparison, the same tests were carried out by using a blocked urethane of biuret derivative of hexamethylene diisocyanate, OLESTER NP-1060-PB (Trade mark of Mitsui Toatsu Chemicals Inc.) Properties of the composition and applied films are illustrated in Table 2.

As illustrated above, polyurethane paints are generally excellent in adhesion to various substrates, balance of hardness and flexibility, crack resistance, water resistance, chemical resistance, gloss and appearance. The paint film prepared from the composition of the invention has outstanding weatherability, light stability and heat stability in addition to these excellent properties, and further has prominent properties as compared with other polyurethane paints available in the market. For example, the polyisocyanatoisocyanurate for use in the non yellowing type urethane paint resin of the invention has high reactivity and heat resistance as compared with polyisocyanate derived from aliphatic isocyanates such as hexamethylene diisocyanate. Hence the resin of the invention has quick drying ability in the initial stage of curing and yellowing tendency in the baking step can be remarkably improved. The resin of the invention also has good compatibility excellent appearance, and equivalent on superior film properties to the conventional resin. Consequently, the resin composition of the invention is suitable for uses such as coating of vehicles where workability, appearance and paint film properties are required.

EXAMPLE 20

Synthesis of Blocked Isocyanate-1

A reaction vessel was replaced by nitrogen, and 134 parts of trimethylolpropane and 300 parts of ethyl acetate were charged. The mixture was heated to 80° C. with stirring.

Further 556 parts of the above BCHI were added over an hour. After finishing the addition, the resultant mixture was reacted at 80° C. for 10 hours. Thereafter 276 parts of ε-caprolactum was charged and further reacted at 80° C. for 4 hours. The reaction mixture was distilled with a Smith distillation apparatus to obtain blocked isocyanate-1 as solid.

EXAMPLE 21

Synthesis of Blocked Isocyanate-2

A reaction vessel was replaced by nitrogen and 167 parts of xylene and 500 parts of BCHI were charged. The mixture was heated to 115° C. with stirring and steam was blown through the mixture. When the isocyanate content was decreased to 18%, the mixture was cooled to 50° C. and 254 parts of methyl ethyl ketone oxime was added dropwise over an hour and further reacted at 50° C. for an hour. The resulting solution was distilled with a Smith distillation apparatus to obtain blocked isocyanate-2 as solid.

EXAMPLE 22

A reaction vessel was replaced by nitrogen, and 500 parts of butyl acetate, 500 parts of BCHI and 3.8 parts of catalyst-A were charged. The mixture was reacted at 80° C. for 4 hours with stirring to obtain polyisocyanato-isocyanurate having an isocyanate content of 6%. Thus obtained solution was mixed with 165 parts of ε-caprolactam and reacted at 110° C. for 4 hours. The reaction mixture was distilled with a Smith distillation apparatus to obtain blocked isocyanate-3 as solid.

EXAMPLE 23 AND COMPARATIVE EXAMPLE 11

Example 23 was carried out by using, as a primary component, polyester resin, Elitel ER-6610(trade mark of Nippon Ester Co. Ltd.), having a hydroxyl value of 31 KOHmg/g. The polyester resin was used in combination with blocked isocyanates 1-3 which were prepared in Examples 20-22.

Comparative Example 11 was carried out by using blocked IPDI, B-1530 (Trade mark of Chemische Werke huls AG).

formulation was carried out as illustrated in Table 2 and mixed in a Henckel mixer and followed by melt-kneeding with a twin screw kneader. The paint mass thus obtained was pulverized and sieved to prepare powder paint. Thus-obtained powder paint was electrostatically spray coated on a zinc phosphate treated iron plate with an electrostatic coating machine and baked for 20 minutes at 160° C. and 180° C., respectively. The film thickness obtained was 70±5 μm.

As illustrated in Table 3, systems cured by simultaneous use of a conventional catalyst required baking temperature of 180° C. or more. In the case of using blocked isocyanate prepared from 2,5 and/or 2.6 diisocyanatomethyl-bicyclo [2,2,1] heptane for the curing agent of powder paint, decreased temperature baking can be carried out at 160° C.

TABLE 1

|  | Test method | Example 11 | Example 12 | Example 13 | Example 14 |
|---|---|---|---|---|---|
| Formulation |  |  |  |  |  |
| Isocyanate component | — | Example 1 | Example 2 | Example 3 | Example 9 |
| Active hydrogen component | — | OLESTER Q-182 | ← | ← | ← |
| solubility | — | good | good | good | good |
| Reactivity |  |  |  |  |  |
| Tack free time (min) | — | 6 | 10 | 13 | 8 |
| Curing time (min) | — | 44 | 48 | 52 | 42 |
| Pot life (hr) | — | 24< | 24< | 24< | 24< |
| Film property |  |  |  |  |  |
| Appearance | — | good | good | good | good |
| Thickness (μm) | — | 24.1 | 24.8 | 25.3 | 23.2 |
| Gloss (60° gloss) | (7) | 87.5 | 82.8 | 82.4 | 89.3 |
| Erichser extrusion (cm) | (2) | 5.23 | 6.4 | 6.7 | 3.75 |
| Du Pont impact (½ in/500 g) | (8) | 30 | 45 | 35 | 20 |
| Magic staining (red) | (3) | ○ | ○ | ○ | ○ |
| (black) |  | Δ | Δ | Δ | Δ |
| (blue) |  | Δ | Δ | Δ | Δ |
| Xylene rubbing (50 cycles) | (4) | ○ | ○ | ○ | ○ |
| Adhesion | (1) | 100/100 | 100/100 | 100/100 | 100/100 |
| Pencil hardness | — | 2 H | 2 H | 2 H | 2 H |
| Resistance to acid | (5) | ○ | ○ | ○ | ○ |
| Resistance to alkali | (5) | ○ | ○ | ○ | ○ |

TABLE 1-continued

| Secondary physical properties | | | | | |
|---|---|---|---|---|---|
| Appearance | — | no change | no change | no change | no change |
| Gloss (60° gloss) | (7) | 88.3 | 85.7 | 83.4 | 86.1 |
| Erichser extrusion (cm) | (2) | 4.43 | 4.01 | 4.35 | 0.70 |
| Du Pont impact (½ in/500 g) | (8) | 35 | 40 | 30 | 30 |
| Adhesion | (1) | 100/100 | 100/100 | 100/100 | 100/100 |
| WOM degree of yellowing (ΔE) | (6) | | | | |
| 200 hrs | | 0.40 | 0.43 | 0.49 | 0.39 |
| 500 hrs | | 0.62 | 0.65 | 0.70 | 0.60 |
| 1000 hrs | | 1.85 | 1.90 | 2.03 | 1.82 |

| | Test method | Comparative Example 2 | Comparative Example 3 | Comparative Example 4 | Comparative Example 5 |
|---|---|---|---|---|---|
| Formulation | | | | | |
| Isocyanate component | — | Comparative Example 1 | OLESTER NP-1000 | COLONATE EH | IPDI T-1890 |
| Active hydrogen component | — | OLESTER Q-182 | ← | ← | ← |
| solubility | — | good | good | good | good |
| Reactivity | | | | | |
| Tack free time (min) | — | 20 | 21 | 19 | 17 |
| Curing time (min) | — | 53 | 60 | 58 | 56 |
| Pot life (hr) | — | 24< | 24< | 24< | 24< |
| Film property | | | | | |
| Appearance | — | good | good | good | good |
| Thickness (μm) | — | 26.3 | 23.0 | 25.5 | 24.1 |
| Gloss (60° gloss) | (7) | 83.4 | 89.1 | 81.7 | 84.2 |
| Erichser extrusion (cm) | (2) | 6.0 | 6.12 | 5.51 | 0.15 |
| Du Pont impact (½ in/500 g) | (8) | 30 | 35 | 30 | 5 |
| Magic staining (red) | (3) | Δ | ○ | ○ | X |
| (black) | | X | Δ | Δ | X |
| (blue) | | Δ | Δ | Δ | X |
| Xylene rubbing (50 cycles) | (4) | Δ | ○ | ○ | Δ |
| Adhesion | (1) | 100/100 | 100/100 | 100/100 | 50/100 |
| Pencil hardness | — | 2 H | 2 H | 2 H | H |
| Resistance to acid | (5) | ○ | ○ | ○ | ○ |
| Resistance to alkali | (5) | ○ | ○ | ○ | ○ |
| Secondary physical properties | | | | | |
| Appearance | — | no change | no change | no change | no change |
| Gloss (60° gloss) | (7) | 82.0 | 87.9 | 82.9 | 85.4 |
| Erichser extrusion (cm) | (2) | 1.73 | 3.39 | 4.51 | 0.27 |
| Du Pont impact (½ in/500 g) | (8) | 20 | 35 | 35 | 20 |
| Adhesion | (1) | 80/100 | 100/100 | 100/100 | 10/100 |
| WOM degree of yellowing (ΔE) | (6) | 0.47 | 0.35 | 0.42 | 0.53 |
| | | 0.70 | 0.78 | 0.65 | 0.82 |
| | | 2.18 | 2.15 | 1.88 | 2.25 |

TABLE 2

| | Test method | Example 15 | Example 16 | Example 17 | Example 18 | Comparative Example 6 |
|---|---|---|---|---|---|---|
| Formulation | | | | | | |
| Isocyanate component | — | Example 1 | Example 2 | Example 3 | Example 9 | Comparative Example 1 |
| Active hydrogen component | — | OLESTER Q-173 | ← | ← | ← | ← |
| compatibility | — | good | good | good | good | good |
| Film property | | | | | | |
| Appearance | — | good | good | good | good | good |
| Yellowing degree | — | 0.33 | 0.42 | 0.50 | 0.21 | 0.40 |
| Film thickness (μm) | (7) | 25.0 | 26.3 | 29.1 | 27.5 | 23.8 |
| Gloss (60° gloss) | (2) | 98.2 | 98.4 | 98.1 | 98.3 | 98.3 |
| Erichser extrusion (cm) | | 8< | 8< | 8< | 8< | 8< |
| Du Pont impact (½ in/500 g) | (8) | 50< | 50< | 50< | 50< | 50< |
| Magic staining (red) | (3) | ○ | ○ | Δ | ○ | Δ |
| (black) | | ○ | ○ | Δ | ○ | Δ |
| (blue) | | ○ | ○ | ○ | ○ | Δ |
| Xylene rubbing (50 cycles) | (4) | ○ | ○ | ○ | ○ | ○ |
| Adhesion | (1) | 100/100 | 100/100 | 100/100 | 100/100 | 100/100 |
| Pencil hardness | — | F | F | F | HB | HB |
| Resistance to acid | (5) | ○ | ○ | ○ | ○ | ○ |
| Resistance to alkali | (5) | ○ | ○ | ○ | ○ | ○ |
| Secondary physical properties | | | | | | |
| Appearance | — | no change | no change | no change | no change | no change |
| Gloss (60° gloss) | (7) | 97.0 | 96.8 | 96.2 | 97.5 | 96.2 |
| Erichser extrusion (cm) | (2) | 8< | 8< | 8< | 8< | 8< |
| Du Pont impact (½ in/500 g) | (8) | 50< | 50< | 50< | 50< | 50< |
| Adhesion | (1) | 100/100 | 100/100 | 100/100 | 100/100 | 100/100 |

TABLE 2-continued

| | Test method | Compar. Example 7 | Compar. Example 8 | Compar. Example 9 | Example 19 | Comparative Example 10 |
|---|---|---|---|---|---|---|
| Formulation | | | | | | |
| Isocyanate component | | — | OLESTER NP-1000 | COLONATE EH | IPDI T-1890 | Example 10 | OLESTER NP-1060-PB |
| Active hydrogen component | | — | OLESTER Q-173 | — | — | Acryl polyol of ref. exam. 2 and base enamel of ref. Exam. 3 | — |
| compatibility | | — | good | good | good | good | good |
| Film property | | | | | | |
| Appearance | | — | good | good | good | good | good |
| Yellowing degree | | — | 0.75 | 0.53 | 0.38 | 0.35 | 0.79 |
| Film thickness (μm) | (7) | 25.4 | 26.0 | 25.9 | 25.1 | 26.2 |
| Gloss (60° gloss) | (2) | 98.9 | 98.0 | 98.5 | 90.9 | 91.3 |
| Erichser extrusion (cm) | | 8< | 8< | 8< | 8< | 8< |
| Du Pont impact (½ in/500 g) | (8) | 50< | 50< | 50< | 50< | 50< |
| Magic staining (red) | (3) | Δ | Δ | Δ | ○ | Δ |
| (black) | | Δ | Δ | Δ | ○ | ○ |
| (blue) | | Δ | ○ | Δ | ○ | ○ |
| Xylene rubbing (50 cycles) | (4) | ○ | ○ | Δ | ○ | ○ |
| Adhesion | (1) | 100/100 | 100/100 | 50/100 | 100/100 | 100/100 |
| Pencil hardness | | — | 2 H | 2 H | H | 2 H | H |
| Resistance to acid | (5) | ○ | ○ | ○ | ○ | ○ |
| Resistance to alkali | (5) | ○ | ○ | ○ | ○ | ○ |
| Secondary physical properties | | | | | | |
| Appearance | | — | no change | no change | no change | no change | no change |
| Gloss (60° gloss) | (7) | 97.3 | 96.2 | 96.2 | 90.1 | 90.0 |
| Erichser extrusion (cm) | (2) | 8< | 8< | 8< | 2.57 | 1.02 |
| Du Pont impact (½ in/500 g) | (8) | 50< | 50< | 50< | 35 | 30 |
| Adhesion | (1) | 100/100 | 100/100 | 100/100 | 100/100 | 100/100 |

TABLE 3

| | | Example 23 | | Com. example 11 |
|---|---|---|---|---|
| Isocyanate component | Example 20 | Example 21 | Example 22 | B-1530 |
| Elitel ER-6610 | 49.1 | 52.4 | 47.8 | 51.9 |
| Blocked isocyanate-1 | 10.9 | — | — | — |
| Blocked isocyanate-2 | — | 7.6 | — | — |
| Blocked isocyanate-3 | — | — | 12.2 | — |
| B-1530 | — | — | — | 8.1 |
| Titague CR-90 (1) | 40 | 40 | 40 | 40 |
| Resimix RL-4 (2) | 1.0 | 1.0 | 1.0 | 1.0 |
| dibuttyltindilaurate | 1.0 | 1.0 | 1.0 | 1.0 |
| Baking. 160° C. × 20 min. | | | | |
| Du Pont impact (cm) (3) | 50< | 50< | 50< | 20 |
| Xylene Rubbing (cycles) (4) | 50< | 50< | 50< | 25 |
| Wetherability (hr) (5) | 600 | 550 | 670 | 200 |
| Erichser extrusion (mm) | 7< | 7< | 7< | 4 |
| Baking. 180° C. × 20 min. | | | | |
| Du Pont impact (cm) (3) | 50< | 50< | 50< | 50< |
| Xylene Rubbing (cycles) (4) | 50< | 50< | 50< | 50< |
| Wetherability (hr) (5) | 600 | 600 | 700 | 450 |
| Erichser extrusion (mm) | 7< | 7< | 7< | 7< |

Note:
(1) Titanium dioxide manufactured by Ishihara Sangyo Co. Ltd.
(2) A leveling agent manufactured by Mitsui Toatsu Chemicals Inc.
(3) Tested under 1 kg load × ½ inch specimen.
(4) Cycles of rubbing with a gauze containing xylene until coated film is damaged.
(5) Time of acceleration test in sun-shine weather-O-meter when gloss retention rate is reached to 80%.

What is claimed is:

1. A polyisocyanato-isocyanurate mixture comprising two or more polyisocyanato-isocyanurates represented by the formula (I):

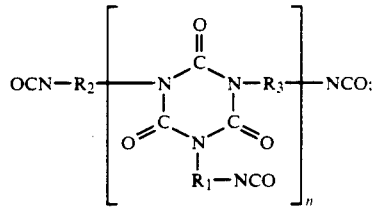

(I)

wherein $R_1$, $R_2$ and $R_3$ are the same or different and are an alkylene group having from 2 to 12 carbon atoms or a group represented by the formula (II):

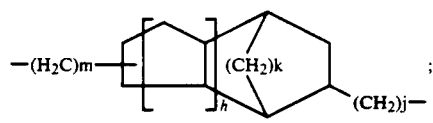

(II)

wherein k is an integer of from 0 to 2, j and m are integers of from 1 to 5 and h is an integer of from 0 to 2, and n is an integer of from 1 to 5, said mixture obtained by reacting a straight chain aliphatic diisocyanate represented by the formula (III):

$$OCN-R_4-NCO \qquad (III)$$

wherein $R_4$ is an alkylene group of from 2 to 12 carbon atoms, with a polycyclo-aliphatic diisocyanate represented by the formula (IV):

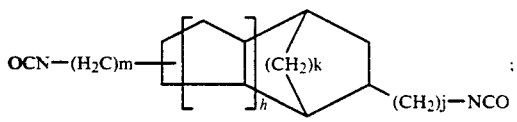  (IV)

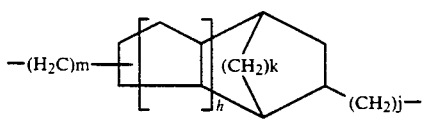  (II)

wherein k is an integer of from 0 to 2, j and m are an integer of from 1 to 5, and h is an integer of from 0 to 2.

2. The polyisocyanato-isocyanurate mixture of claim 1, wherein n is an integer of 1 in the formula (I).

3. The polyisocyanato-isocyanurate mixture of claim 1, wherein n is an integer of from 2 to 5 in the formula (I).

4. The polyisocyanato-isocyanurate mixture of claim 1, wherein the mixture of the formula (I) comprises from 30% to 90% by weight of the polyisocyanato-isocyanurate having the integer n of 1 and from 10 to 70% by weight of the polyisocyanato-isocyanurate having the integer n of from 2 to 5.

5. The polyisocyanato-isocyanurate mixture of claim 1, wherein the straight chain aliphatic diisocyanate is hexamethylene diisocyanate.

6. The polyisocyanato-isocyanurate mixture of claim 1, wherein the polycyclo-aliphatic diisocyanate represented by the formula (IV) is 2,5-or 2,6-diisocyanatomethylbicyclo (2,2,1) heptane or a mixture of the same.

7. The polyisocyanato-isocyanurate mixture of claim 1, wherein the straight chain aliphatic diisocyanate represented by the formula (III) is hexamethylene diisocyanate and the polycyclo-aliphatic diisocyanate represented by the formula (IV) is 2,5- or 2,6-diisocyanatomethyl-bicyclo (2,2,1) heptane or a mixture of the same.

8. An essentially single polyisocyanato-isocyanurate represented by the formula (I) according to claim 1, wherein n is 1, one or more of $R_1$, $R_2$ and $R_3$ are a group represented by the formula (II):

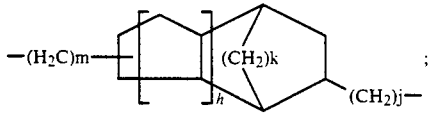  (II)

wherein k is an integer of from 0 to 2, j and m are an integer of from 1 to 5 and h is an integer of from 0 to 2, and the remainder is an alkylene group having from 2 to 12 carbon atoms.

9. A preparation process of a polyisocyanato-isocyanurate mixture comprising two or more polyisocyanato-isocyanurate represented by the formula (I):

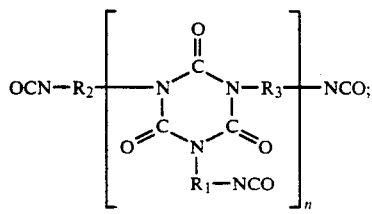  (I)

wherein $R_1$, $R_2$ and $R_3$ are the same or different and are an alkylene group having from 2 to 12 carbon atoms or a group represented by the formula (II):

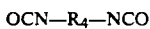  (II)

wherein k is an integer of from 0 to 2, j and m are an integer of from 1 to 5, and h is an integer of from 0 to 2, and n is an integer of from 1 to 5, said process comprising the steps of (i) trimerizing a portion of isocyanate groups in a mixture of the straight chain aliphatic diisocyanate represented by the formula (III)

$$OCN-R_4-NCO \quad (III);$$

wherein $R_4$ is an alkylene group of from 2 to 12 carbon atoms, and a polyccyclo-aliphatic diisocyanate represented by the formula (IV)

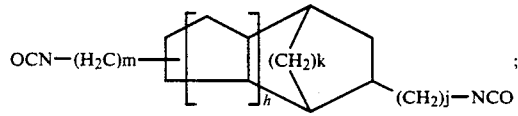  (IV)

wherein k is a integer of from 0 to 2, j and m are an integer of from 1 to 5, and h is an integer of from 0 to 2, in a mole ratio of from about 1:11 to 11:1 in the presence of a trimerization catalyst until trimerizing about 20 to 50% of initially present isocyanate groups; (ii) immediately adding a catalyst poison to terminate the trimerization reaction by deactivating the trimerization catalyst; and (iii) removing unreacted diisocyanate.

10. The preparation process of claim 9, wherein the trimerization catalyst is a combination of an alkali metal compound salt of a carboxylic acid and a polyethyleneoxide compound or an alcohol.

11. The preparation process of claim 9, wherein the straight chain aliphatic diisocyanate represented by the formula (iii) is hexamethylene diisocyanate.

12. The preparation process of claim 9, wherein the polycyclo-aliphatic diisocyanate represented by the formula (IV) is 2,5- or 2,6-diisocyanatomethylbicyclo (2,2,1) heptane or a mixture of the same.

13. The preparation process of claim 9, wherein the straight chain aliphatic diisocyanate represented by the formula (III) is hexamethylene diisocyanate and the polycyclo-aliphatic diisocyanate represented by the formula (IV) is 2,5- or 2,6-diisocyanatomethylbicyclo (2,2,1) heptane or a mixture of the same.

14. A non-yellowing type urethane paint resin comprising a polyisocyanato-isocyanurate mixture of formula (I) according to claim 1 as a curing agent and a two or more active hydrogen containing compounds as a main component.

15. A non-yellowing type urethane paint resin comprising a polyisocyanato-isocyanurate mixture according to claim 1 as a curing agent and a two or more active hydrogen containing compounds as a main component.

16. A non-yellowing type urethane paint resin comprising a polyisocyanato-isocyanurate according to claim 8 as a curing agent and a two or more active hydrogen containing compounds as a main compound.

17. The non-yellowing type urethane paint resin of claim 16, wherein the proportion of the polyisocyanato-isocyanurate mixture to the two or more active hydrogen containing compounds is a H/NCO equivalent ratio of from 0.8 to 1.2.

18. A paint composition comprising a non-yellowing type urethane paint resin according to claim 16.

19. A curing agent for a urethane paint resin obtained by blocking an isocyanate group of a polyisocyanato-isocyanurate mixture of the formula (I) according to claim 1 with a compound having one or more active hydrogen(s) is a molecule.

20. A curing agent for a urethane paint resin obtained by blocking an isocyanate group of a polyisocyanato-isocyanurate according to claim 8 with a compound having one or more active hydrogen(s) in a molecule.

21. A non-yellowing type urethane paint resin composition comprising a curing agent for a urethane paint resin according to claim 20.

22. A powder-paint curing agent obtained by blocking 2,5- or 2,6-diisocyanatomethylbicyclo [2,2,1] heptane or a mixture of the same with a compound having one or more active hydrogen atoms in a molecule.

23. A powder-paint curing agent obtained by blocking a modified 2,5- or 2,6-diisocyanatomethylbicyclo [2,2,1] heptane with a compound having one or more active hydrogen in a molecule.

24. The powder-paint curing agent of claim 23, wherein the modified product is an active-isocyanate-group containing urethane polymer obtained by reacting 2,5- or 2,6 -diisocyanatomethylbicyclo (2,2,1) heptane or a mixture of the same with water, diol or polyol.

25. The powder-paint curing agent of claim 23, wherein the modified product is a polyisocyanate having an isocyanurate linkage obtained by trimerization of 2,5- or 2,6, -diisocyanatomethylbicyclo (2,2,1) heptane or a mixture of the same.

26. A polyester powder-paint composition comprising a powder-paint curing agent according to claim 25 and polyester polyol in an equivalent ratio of active hydrogen (H) in the polyester polyol to a blocked isocyanate group (NCO) in the curing agent to be dissociated at the baking temperature, of from 0.8 to 1.3.

27. The non-yellowing type urethane paint resin of claim 15, wherein the proportion of the polyisocyanato-isocyanurate mixture to the two or more active hydrogen containing compounds is a H/NCO equivalent ratio of from 0.8 to 1.2

28. The non-yellowing type urethane paint resin of claim 14, wherein the proportion of the polyisocyanato-isocyanurate mixture to the two or more active hydrogen containing compounds is a H/NCO equivalent ratio of from 0.8 to 1.2

29. A paint composition comprising the non-yellowing type urethane paint resin of claim 15.

30. A paint composition comprising the non-yellowing type urethane paint resin of claim 14.

31. A non-yellowing type urethane paint resin composition comprising a curing agent for urethane paint resin according to claim 1.

32. A non-yellowing type urethane paint resin composition comprising a curing agent for urethane paint resin according to claim 19.

33. A polyester powder-paint composition comprising powder-paint curing agent according to claim 24 and polyester polyol in an equivalent ratio of active hydrogen (H) in the polyester polyol to a blocked isocyanate group (NCO) in the curing agent to be dissociated at the baking temperature, of from 0.8 to 1.3

34. A polyester powder-paint composition comprising a powder-paint curing agent of according to claim 23 and polyester polyol in an equivalent ratio of active hydrogen (H) in the polyester polyol to a blocked isocyanate group (NCO) in the curing agent to be dissociated at the baking temperature, of from 0.8 to 1.3.

35. A polyester powder-paint composition comprising a powder-paint curing agent according to claim 22 and polyester polyol in an equivalent ratio of active hydrogen (H) in the polyester polyol to a blocked isocyanate group (NCO) in the curing agent to be dissociated at the baking temperature, of from 0.8 to 1.3.

* * * * *